US00PP22305P2

(12) United States Plant Patent
Bergman

(10) Patent No.: US PP22,305 P2
(45) Date of Patent: Dec. 6, 2011

(54) ***CHRYSANTHEMUM* PLANT NAMED 'SYNCIN PUEBLO'**

(50) Latin Name: *Chrysanthemum×morifolium*
Varietal Denomination: Syncin Pueblo

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/802,378

(22) Filed: Jun. 4, 2010

(51) Int. Cl.
*A01H 5/00* (2006.01)

(52) U.S. Cl. ..... Plt./296

(58) Field of Classification Search ..... Plt./296, Plt./286
See application file for complete search history.

(56) References Cited

OTHER PUBLICATIONS

Dana et al. *Chrysanthemums.* Purdue University Cooperative Extension Service, RR 9/96 (1996) HO-77, 2 pages.*

* cited by examiner

*Primary Examiner* — June Hwu
(74) *Attorney, Agent, or Firm* — S. Matthew Edwards

(57) ABSTRACT

A new *Chrysanthemum* plant named 'Syncin Pueblo' particularly distinguished by the greyed-orange ray floret color with mostly green discs at the early age, single, daisy-type flowers, strong stems, good shelf-life, medium green foliage, uniform plant habit and flowering response time, and about an 8 week flowering response time.

1 Drawing Sheet

Latin name of the genus and species of the plant claimed: *Chrysanthemum×morifolium.*

Varietal denomination: 'Syncin Pueblo'.

BACKGROUND OF THE NEW PLANT

The present invention comprises a new *Chrysanthemum*, botanically known as *Chrysanthemum×morifolium*, and hereinafter referred to by the variety name 'Syncin Pueblo'.

'Syncin Pueblo' is a product of a planned breeding program. The new cultivar has greyed-orange ray floret color with mostly green discs at the early age, single, daisy-type flowers, strong stems, good shelf-life, medium green foliage, uniform plant habit and flowering response time, and about an 8 week flowering response time.

'Syncin Pueblo' originates as a natural whole plant mutation of 'Yopueblo', U.S. Plant Pat. No. 20,546. 'Syncin Pueblo' was discovered and selected by the inventor as a single flowering plant within a population of the parent cultivar in a field trial in Fort Myers, Fla. in March 2008. The parent cultivar 'Yopueblo' has a lighter orange ray floret color.

The first act of asexual reproduction of 'Syncin Pueblo' was accomplished when vegetative cuttings were propagated from the initial selection in June 2008 in a controlled environment in Fort Myers, Fla.

BRIEF SUMMARY OF INVENTION

Horticultural examination of plants grown from cuttings of the plant initiated in June 2008, and continuing thereafter, has demonstrated that the combination of characteristics as herein disclosed for 'Syncin Pueblo' are firmly fixed and are retained through successive generations of asexual reproduction.

'Syncin Pueblo' has not been observed under all possible environmental conditions. The phenotype may vary significantly with variations in environment such as temperature, light intensity and day length.

A Plant Breeder's Right for this cultivar was applied for in Canada on Oct. 30, 2009 (#09-6762). 'Syncin Pueblo' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Syncin Pueblo' with colors being as true as possible with an illustration of this type. The photographic drawing shows four flowering plants of the new variety growing in one 6 inch pot and a close-up of the flowers.

DETAILED BOTANICAL DESCRIPTION

The plant descriptions, measurements, and aforementioned photographs were taken in Gilroy, Calif. in April 2010 under natural light. These plants were started and grown in Nipomo, Calif. and were shipped to Gilroy in April. Plants were grown under conditions which approximate those generally used in commercial potted *chrysanthemum* production. These plants used in the photograph and descriptions were about 10 weeks old.

Color references are made to The Royal Horticultural Society Colour Chart (R.H.S.) 2001.

TABLE 1

DIFFERENCES BETWEEN THE NEW VARIETY 'SYNCIN PUEBLO' AND A SIMILAR VARIETY

| | 'Syncin Pueblo' | 'Yoauburn' (U.S. Plant Pat. No. 12,526) |
|---|---|---|
| Immature disc color/size: | Greener/larger | More yellow/smaller |
| Ray floret apex shape: | More acute | More mucronulate |
| Inflorescence size: | Little smaller | Little larger |

Plant:

*Form, growth and habit.*—Herbaceous pot-type. Stems are strong, upright and outwardly spreading, good shelf life, uniform plant habit and flowering response, suitable for production using center budded or no bud removal.

*Plant height.*—22-23 cm.

*Plant height (inflorescence included).*—25-28 cm.

*Plant width.*—About 40 cm.

Roots:

*Number of days to initiate roots.*—4 days at about 22 degrees C.

*Number of days to produce a rooted cutting.*—10 days at 22 degrees C.

*Type.*—Fine, fibrous, free branching.

*Color.*—RHS N155B but whiter.

Foliage:

*Arrangement.*—Alternate.

*Immature, leaf color, upper surface.*—Closest to RHS 147A but darker.

*Lower surface.*—RHS 147B but lighter.

*Mature, leaf color, upper surface.*—Between RHS 147A but lighter to RHS 146A.

*Lower surface.*—RHS 147B.

*Length.*—7.0-7.5 cm.

*Width.*—4.6-5.5 cm.

*Shape.*—Ovate.

*Base shape.*—Attenuate.

*Apex shape.*—Mucronulate.

*Margin.*—Palmately lobed, slightly crenate.

*Texture, upper surface.*—Bi-fid T-shaped hairs.

*Lower surface.*—Bi-fid T-shaped hairs.

*Color of veins, upper surface.*—RHS 144B.

*Color of veins, lower surface.*—RHS 144B.

*Petiole color.*—RHS 144B.

*Length.*—1.3-1.5 cm.

*Diameter.*—0.3-0.35 cm.

*Texture.*—Bi-fid T-shaped hairs.

Stem:

*Quantity of main branches per plant.*—3-4.

*Color of stem.*—RHS 146B but appears lighter being heavily covered with hairs.

*Length of stem.*—About 20 cm.

*Diameter.*—0.4-0.5 cm.

*Length of internodes.*—1.5-3.5 cm.

*Texture.*—Bi-fid T-shaped hairs.

*Color of peduncle.*—RHS 147B but appears lighter being heavily covered with hairs.

*Length of peduncle.*—4.5-6.5 cm.

*Peduncle diameter.*—0.3 cm.

*Texture.*—Bi-fid T-shaped hairs.

Inflorescence:

*Type.*—Composite type, solitary inflorescences (dasiy-type) borne terminally above foliage, ray florets arranged acropetally on a capitulum.

*Quantity of short days to flowering (response time).*—54-56 days.

*Quantity of inflorescences per plant.*—21-25.

*Lastingness of individual blooms on the plant.*—30 days.

*Fragrance.*—Slight.

Bud (just before opening/showing color):

*Color.*—RHS 166C but a little more tan-brown.

*Length.*—0.5-0.8 cm.

*Width.*—1.5-1.8 cm.

*Shape.*—Oblate.

Immature inflorescence:

*Diameter.*—5.0-5.58 cm.

*Color of ray florets, upper surface.*—RHS 163A heavily overlaid with RHS N172A but more red and RHS N163A with RHS 3A at the very base.

*Lower surface.*—RHS 163B overlaid with RHS N172A to RHS 173A at the margins.

Mature inflorescence:

*Diameter.*—6.5-7.0 cm.

*Depth.*—2.5 cm.

*Total diameter of 'disc'.*—2.0 cm.

*Receptacle height.*—0.5 cm.

*Receptacle diameter.*—0.7-0.8 cm.

Ray florets:

*Average quantity of florets.*—About 30 in numerous whorls.

*Color of florets, upper surface.*—RHS 163A heavily overlaid with RHS N172A but more red and RHS N163A with RHS 3A at the very base.

*Lower surface.*—RHS 163B overlaid with RHS N172A to RHS 173A at the margins.

*Length.*—2.7-3.3 cm.

*Width.*—1.2-1.3 cm.

*Shape.*—Oval to elliptical.

*Apex shape.*—Mucronulate.

*Margin.*—Entire.

*Texture, upper surface.*—Papillose.

*Lower surface.*—Papillose.

Disc florets:

*Average quantity of florets.*—100-140.

*Color of florets.*—RHS 2D with RHS 9A apex.

*Length.*—0.6 cm.

*Width.*—0.1 cm.

*Shape.*—Tubular, elongated.

*Apex shape.*—Acute, 5 pointed.

Phyllaries:

*Quantity.*—About 24.

*Color, upper surface.*—RHS 137B.

*Lower surface.*—RHS 137B but appears lighter and greyer being heavily covered with hairs.

*Length.*—0.4-0.6 cm.

*Width.*—0.15-0.2 cm.

*Shape.*—Lanceolate.

*Apex shape.*—Acute.

*Based.*—Fused.

*Margins.*—Entire, papery.

*Texture, upper surface.*—Glossy and glabrous.

*Lower surface.*—Bi-fid T-shaped hairs.

Reproductive organs:

*Found on both florets.*—Pistil: 1. Length: 0.6-0.7 cm. Style color: RHS 9C. Style length: 0.5-0.6 cm. Stigma color: RHS 9A. Stigma shape: Bi-parted. Ovary color: Not observed.

*Found on only disc florets.*—Stamens: 1. Color of filaments: RHS 1B but more translucent green. Length filaments: 0.3 cm. Anther color: RHA 14B. Anther length: 0.15-0.2 cm. Anther shape: Oblong. Color of pollen: RHS 14A. Pollen amount: Poor to moderate. Fertility/seed set: Has not been observed on this hybrid.

Disease/pest resistance: Disease/pest resistance has not been observed on this hybrid.

What is claimed is:

1. A new and distinct variety of *Chrysanthemum* plant named 'Syncin Pueblo' substantially as illustrated and described herein.

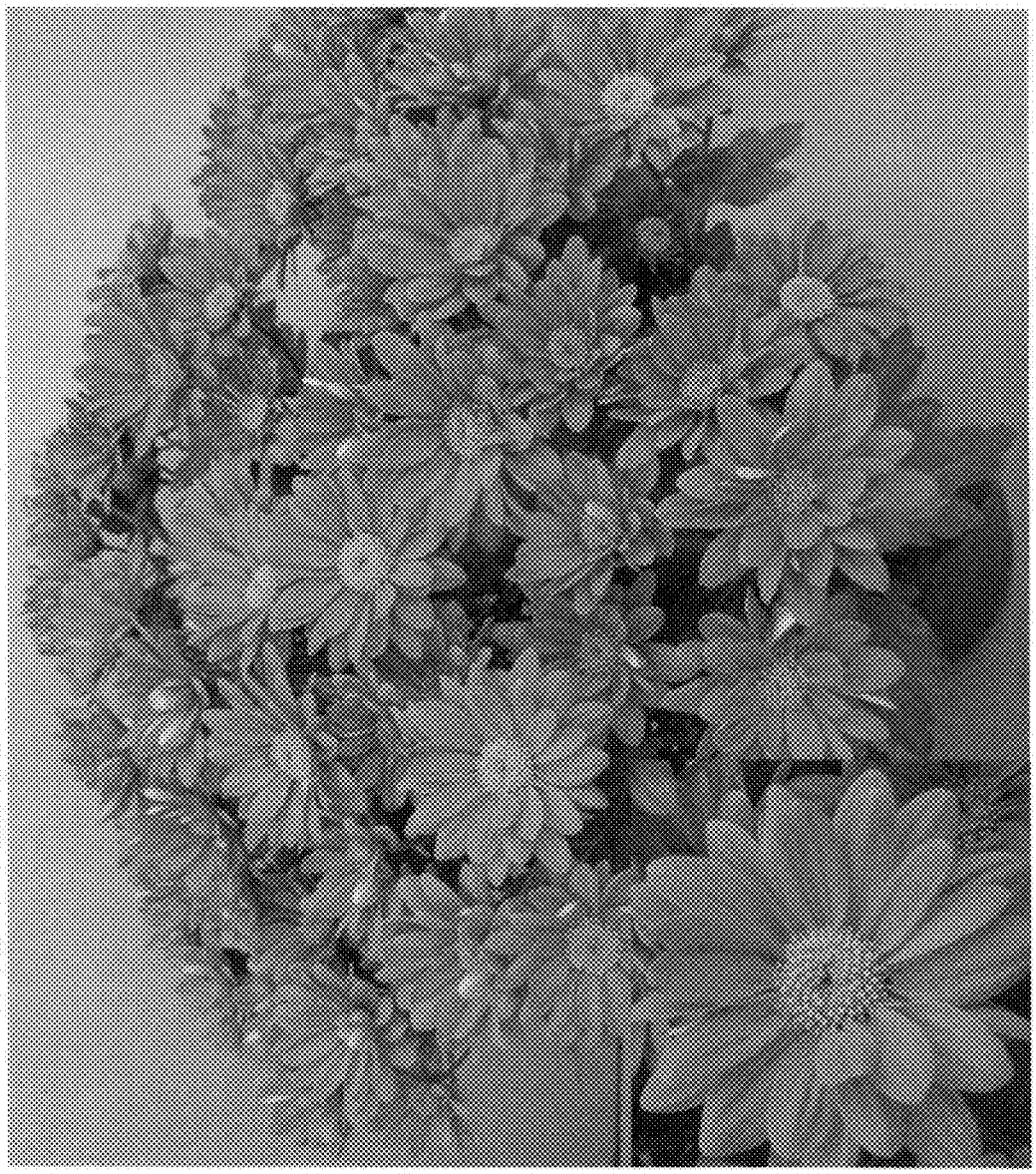

* * * * *